US011446100B2

(12) United States Patent
Betsugi et al.

(10) Patent No.: US 11,446,100 B2
(45) Date of Patent: Sep. 20, 2022

(54) SURGICAL INSTRUMENT, ROBOTIC SURGICAL SYSTEM, AND METHOD OF DETACHING SURGICAL INSTRUMENT ATTACHED TO ROBOT ARM OF ROBOTIC SURGICAL SYSTEM THROUGH ADAPTOR

(71) Applicant: MEDICAROID CORPORATION, Kobe (JP)

(72) Inventors: Shota Betsugi, Kobe (JP); Yu Usuki, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 669 days.

(21) Appl. No.: 16/549,959

(22) Filed: Aug. 23, 2019

(65) Prior Publication Data

US 2020/0069381 A1    Mar. 5, 2020

(30) Foreign Application Priority Data

Aug. 28, 2018 (JP) .............................. JP2018-159330

(51) Int. Cl.
| | | |
|---|---|---|
| *A61B 34/30* | (2016.01) | |
| *A61B 90/00* | (2016.01) | |
| *A61B 90/50* | (2016.01) | |
| *A61B 46/10* | (2016.01) | |
| *A61B 46/20* | (2016.01) | |
| *A61B 17/00* | (2006.01) | |

(52) U.S. Cl.
CPC .............. *A61B 34/30* (2016.02); *A61B 46/10* (2016.02); *A61B 90/361* (2016.02); *A61B 90/50* (2016.02); *A61B 46/20* (2016.02); *A61B 2017/00477* (2013.01); *A61B 2017/00973* (2013.01); *A61B 2034/305* (2016.02)

(58) Field of Classification Search
CPC combination set(s) only.
See application file for complete search history.

(56) References Cited

U.S. PATENT DOCUMENTS

| | | |
|---|---|---|
| 8,998,930 B2 | 4/2015 | Orban, III |
| 2015/0257841 A1 | 9/2015 | Dachs, II |

FOREIGN PATENT DOCUMENTS

| | | |
|---|---|---|
| EP | 2022416 A2 | 2/2009 |
| EP | 2022416 A3 | 4/2009 |
| WO | 2016/176170 A1 | 11/2016 |
| WO | 2017/205311 A1 | 11/2017 |
| WO | 2018/119136 A1 | 6/2018 |

*Primary Examiner* — Scott Luan
(74) *Attorney, Agent, or Firm* — Metrolex IP Law Group, PLLC

(57) ABSTRACT

A surgical instrument according to an embodiment may include: a base body including an attachment surface for the adaptor; a surgical tool; driven members rotatably provided on the base body; a housing covering the driven members; and first and second movable members movable with respect to the housing and the base body. The attachment surface of the base body includes a first guide groove and a second guide groove that slidably receive a first guide rail and a second guide rail provided on the adaptor respectively. The first and second guide grooves are defined by the base body and the first and second movable members such that groove widths of the first and second guide grooves are variable by moving the first and second movable members with respect to the base body.

20 Claims, 10 Drawing Sheets

SURGICAL INSTRUMENT, ROBOTIC SURGICAL SYSTEM, AND METHOD OF DETACHING SURGICAL INSTRUMENT ATTACHED TO ROBOT ARM OF ROBOTIC SURGICAL SYSTEM THROUGH ADAPTOR

CROSS REFERENCE TO RELATED APPLICATIONS

This application claims priority to Japanese Patent Application No. JP2018-159330 filed on Aug. 28, 2018, the entire contents of which are incorporated herein by reference.

BACKGROUND

The disclosure relates to a surgical instrument, and particularly relates to a surgical instrument that is detachably connected to a robot arm of a robotic surgical system through an adaptor, the robotic surgical system, and a method of detaching the surgical instrument attached to the robot arm of the robotic surgical system through the adaptor.

In a related art, there has been known a surgical instrument that is detachably connected to a robot arm of a robotic surgical system through an adaptor (e.g., see U.S. Pat. No. 8,998,930).

U.S. Pat. No. 8,998,930 discloses a surgical instrument including: a base body that includes tabs to be engaged with a retaining member of an adaptor and that is attached to the adaptor; a surgical tool; an elongated shaft in which one end is connected to the base body and the other end is connected to the surgical tool; and driven members that are rotatably provided on the base body and connected with end portions of elongated elements for operating the surgical tool. For a case of attaching the surgical instrument to the adaptor, the surgical instrument is configured to engage the tabs of the base body with the retaining member of the adaptor by sliding the base body with respect to the adaptor. For a case of detaching the surgical instrument from the adaptor, the surgical instrument is configured to disengage the tabs of the base body from the retaining member of the adaptor by sliding the surgical instrument in the direction opposite to the attachment direction.

SUMMARY

In U.S. Pat. No. 8,998,930, for the case of detaching the surgical instrument from the adaptor, the tabs of the base body are disengaged from the retaining member of the adaptor by sliding the surgical instrument in the direction opposite to the attachment direction. Thus, when the force of the engagement between the tabs and the retaining member is large, large force is required to disengage and detach the surgical instrument from the adaptor. In this case, there is a problem of difficulty in easy attachment and detachment of the surgical instrument to and from the adaptor. On the other hand, when the force of the engagement between the tabs and the retaining member is small, force of fixing the surgical instrument to the adaptor is small. In this case, there is a problem of difficulty in stable fixing of the surgical instrument to the adaptor. As described above, the surgical instrument has a problem of difficulty in achieving both the easy attachment and detachment of the surgical instrument to and from the adaptor and the stable fixing of the surgical instrument to the adaptor.

An embodiment of the disclosure is directed to a surgical instrument that is detachably connected to a robot arm of a robotic surgical system through an adaptor, in which the adaptor can be easily attached to and detached from the adaptor and the surgical instrument can be stably fixed to the adaptor.

A first aspect of the disclosure may be a surgical instrument to be detachably connected to a robot arm of a robotic surgical system through an adaptor. The surgical instrument according to the first aspect may include: a base body that includes an attachment surface for the adaptor; a surgical tool; an elongated shaft in which one end is connected to the base body and the other end is connected to the surgical tool; driven members that are rotatably provided on the base body and connected with end portions of elongated elements to operate the surgical tool; a housing that covers the driven members; and a first movable member and a second movable member that are provided movably with respect to the housing and the base body. The attachment surface of the base body includes a first guide groove and a second guide groove that slidably receive a first guide rail and a second guide rail provided on the adaptor respectively. The first and second guide grooves are defined by the base body and the first and second movable members such that groove widths of the first and second guide grooves are variable by moving the first and second movable members with respect to the base body.

A second aspect of the disclosure may be a robotic surgical system that may include: a robot arm; an adaptor that is attached to the robot arm; and a surgical instrument that is attached to the adaptor. The adaptor may include a first surface that is attached to the robot arm, a second surface to which the surgical instrument is mounted, and a first guide rail and a second guide rail that are provided on the second surface. The surgical instrument may include: a base body that includes an attachment surface attached to the second surface of the adaptor, a surgical tool, an elongated shaft in which one end is connected to the base body and the other end is connected to the surgical tool, driven members that are rotatably provided on the base body and connected with end portions of elongated elements operating the surgical tool; a housing that is provided to cover the driven members; and a first movable member and a second movable member that are provided movably with respect to the housing and the base body. The attachment surface of the base body includes a first guide groove and a second guide groove that slidably receive a first guide rail and a second guide rail provided on the adaptor respectively. The first and second guide grooves are defined by the base body and the first and second movable members such that groove widths of the first and second guide grooves are variable by moving the first and second movable members with respect to the base body.

A third aspect of the disclosure may be a method of detaching a surgical instrument that is attached to a robot arm of a robotic surgical system through an adaptor. The method may include: disengaging the surgical instrument from the adaptor by pressing a movable member of the surgical instrument to move the movable member to increase a groove width of a guide groove of the surgical instrument; and detaching the surgical instrument from the adaptor by sliding the guide groove along a guide rail of the adaptor while pressing the movable member of the surgical instrument.

DETAILED DESCRIPTION

Figure 1:
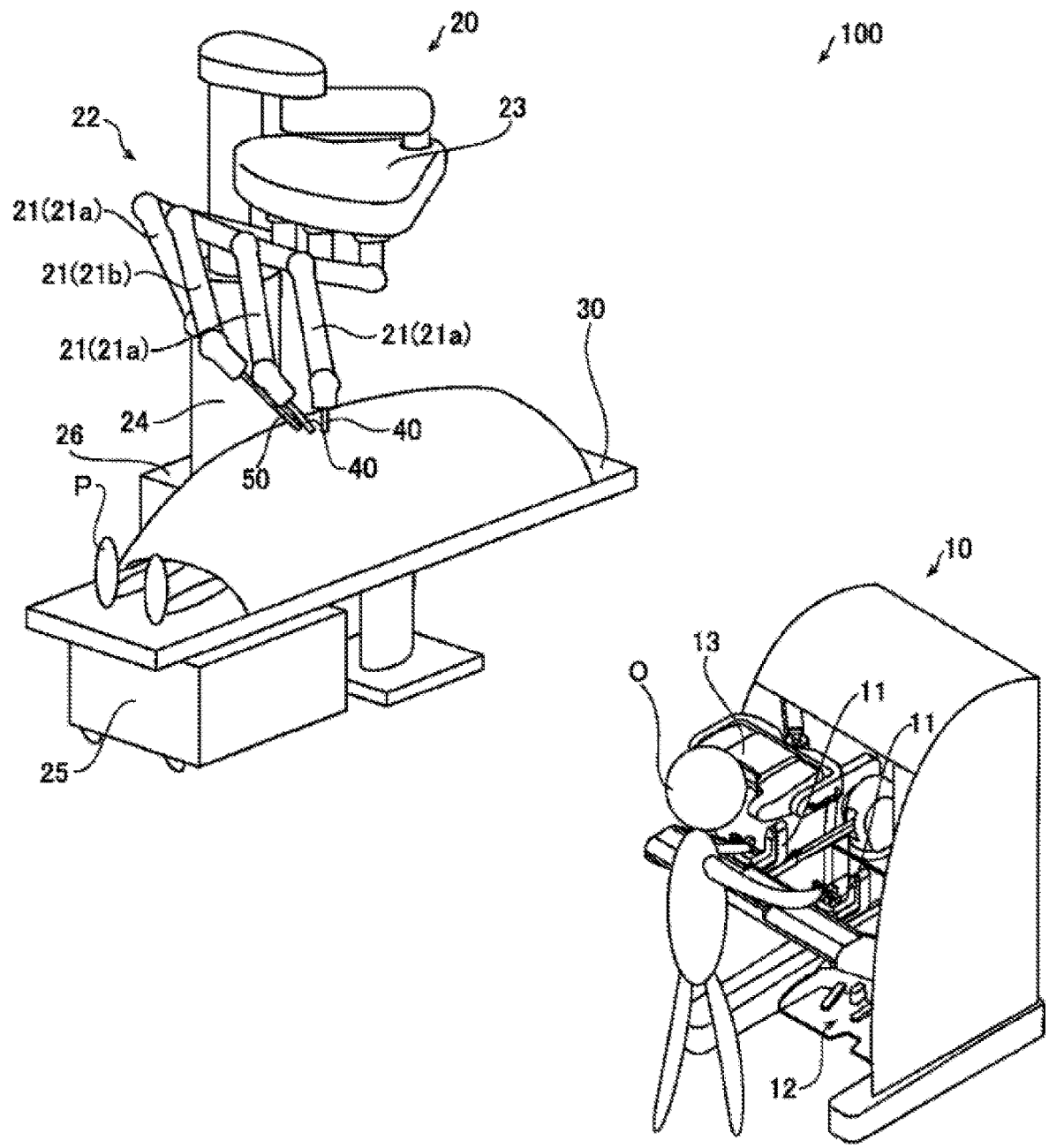
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

The configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 and an endoscope 50, attached to robot arms 21. This allows minimally invasive surgery.

The patient-side apparatus 20 constitutes an interface to perform a surgery on a patient P. The patient-side apparatus 20 is positioned beside an operation table 30 on which the patient P is laid. The patient-side apparatus 20 includes robot arms 21. One of the robot arms 21 (21b) holds the endoscope 50 while the other robot arms 21 (21a) hold the surgical instruments 40. The robot arms 21 are commonly supported by a platform 23. Each of the robot arms 21 includes joints. Each joint includes a driver provided with a servo-motor and a position detector such as an encoder. The robot arms 21 are configured so that the medical equipment attached to each robot arm 21 is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment are detachably attached to the distal ends of the robot arms 21a. Each surgical instrument 40 includes: a housing 43 (see FIG. 4), which is attached to the robot arm 21a; an elongated shaft 42 (see FIG. 4); and an end effector 41 (see FIG. 4), which is provided at the tip of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed, for example.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
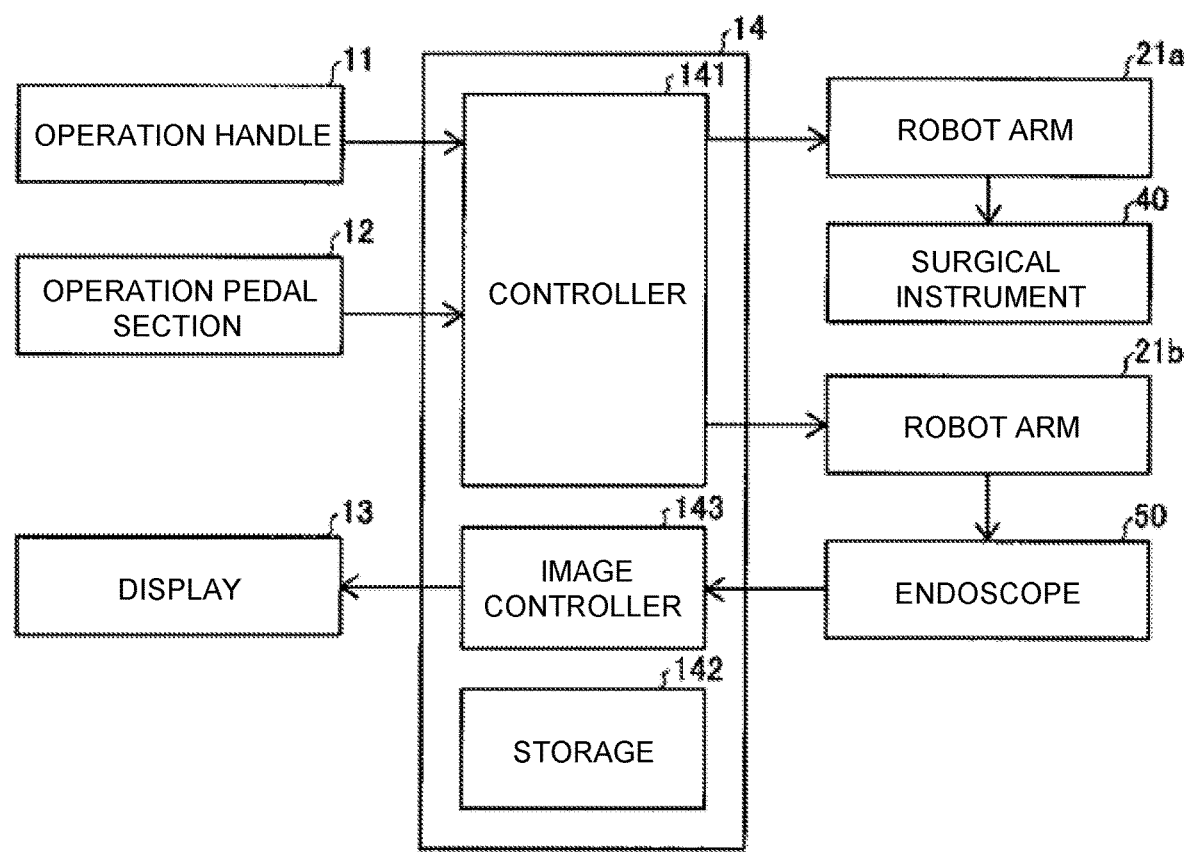
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate medical equipment attached to the robot arms 21. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured to move up and down, right and left, and forward and rearward.

The remote control apparatus 10 and patient-side apparatus 20 constitute a master-slave system in terms of controlling movement of the robot arms 21*a* and robot arm 21*b*. The operation handles 11 constitute an operating section on the master side in the master-slave system, and the robot arms 21*a* and 21*b* holding medical equipment constitute an operating section on the slave side. When the operator O operates the operation handles 11, the movement of one of the robot arms 21*a* or 21*b* is controlled so that the tip (the end effector 41 of the surgical instrument 40) of the robot arm 21*a* or the tip (the endoscope 50) of the robot arm 21*b* moves following the movement of the operation handles 11.

The patient-side apparatus 20 controls the movement of the robot arms 21*a* in accordance with the set motion scaling ratio. When the motion scaling ratio is set to ½, for example, the end effectors 41 of the surgical instruments 40 move ½ of the movement distance of the operation handles 11. This allows precise fine surgery.

The operation pedal section 12 includes pedals to execute medical equipment-related functions. The pedals include a coagulation pedal, a cutting pedal, a camera pedal, and a clutch pedal. The pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21 to stop movement of the surgical instruments 40. Specifically, when the clutch pedal is being pressed, the robot arms 21 of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21. The operator O restarts the operation for the operation handles 11 around the center thereof.

The display section 13 is configured to display images captured by the endoscope 50. The display section 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 50 attached to the robot arm 21*b* of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be formed of a single controller performing centralized control or may be composed of controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed.

(Configurations of Adaptor and Surgical Instrument)

With reference to FIGS. 3 to 14, the configurations of an adaptor 60 and the surgical instrument 40 according to an embodiment are described.

Figure 3:
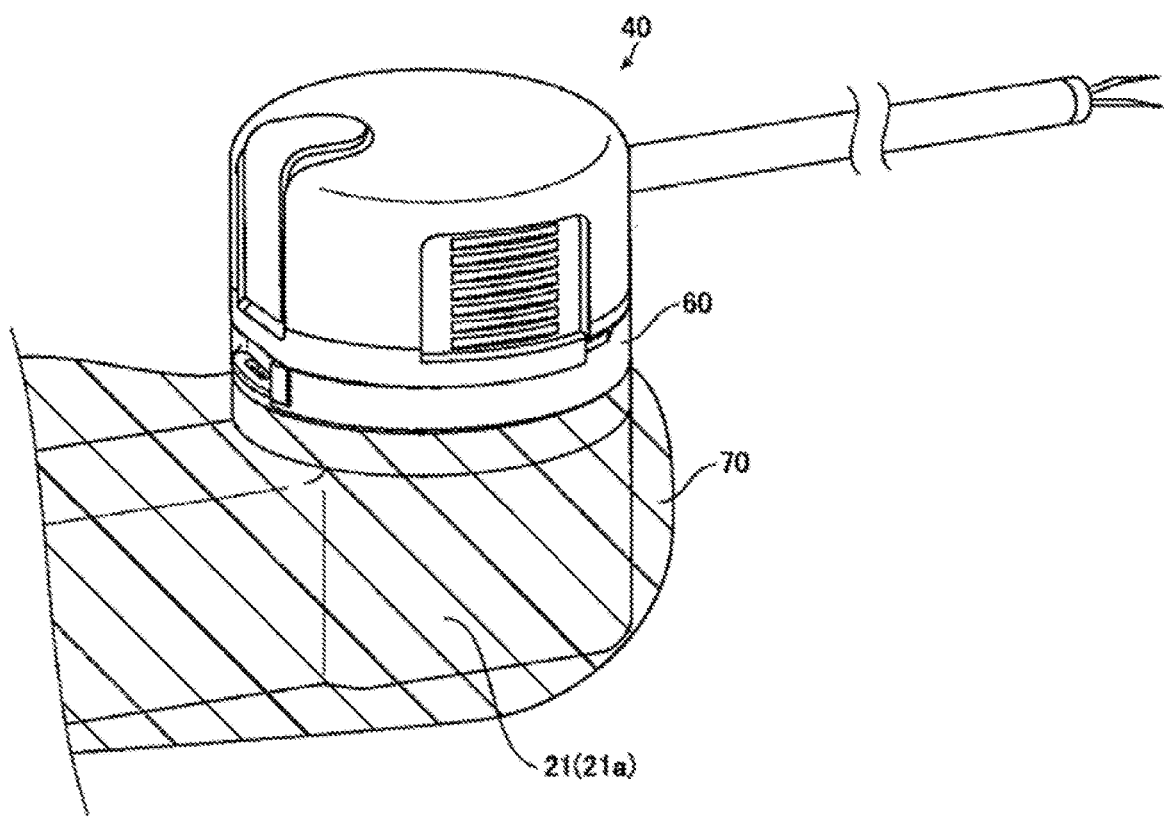
FIG. 3 is a diagram illustrating a perspective view of a state of an embodiment where a surgical instrument is attached to a robot arm through an adaptor.

As illustrated in FIG. 3, the robot arm 21 is used in a clean area and is covered with a drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drapes 70.

The drape 70 is arranged between the robot arm 21 and the surgical instrument 40. Specifically, the drape 70 is arranged between the adaptor 60 and the robot arm 21. The adaptor 60 is attached to the robot arm 21 while putting the drape 70 between the adaptor 60 and the robot arm 21. Specifically, the adaptor 60 is a drape adaptor that puts the drape 70 between the adaptor 60 and the robot arm 21a. The surgical instrument 40 is attached to the adaptor 60 that is attached to the robot arm 21a with the drape 70 interposed therebetween. The robot arm 21 transmits driving force to the surgical instrument 40 through the adaptor 60 to drive the end effector 41 of the surgical instrument 40. The end effector 41 is an example of a surgical tool.

Figure 4:
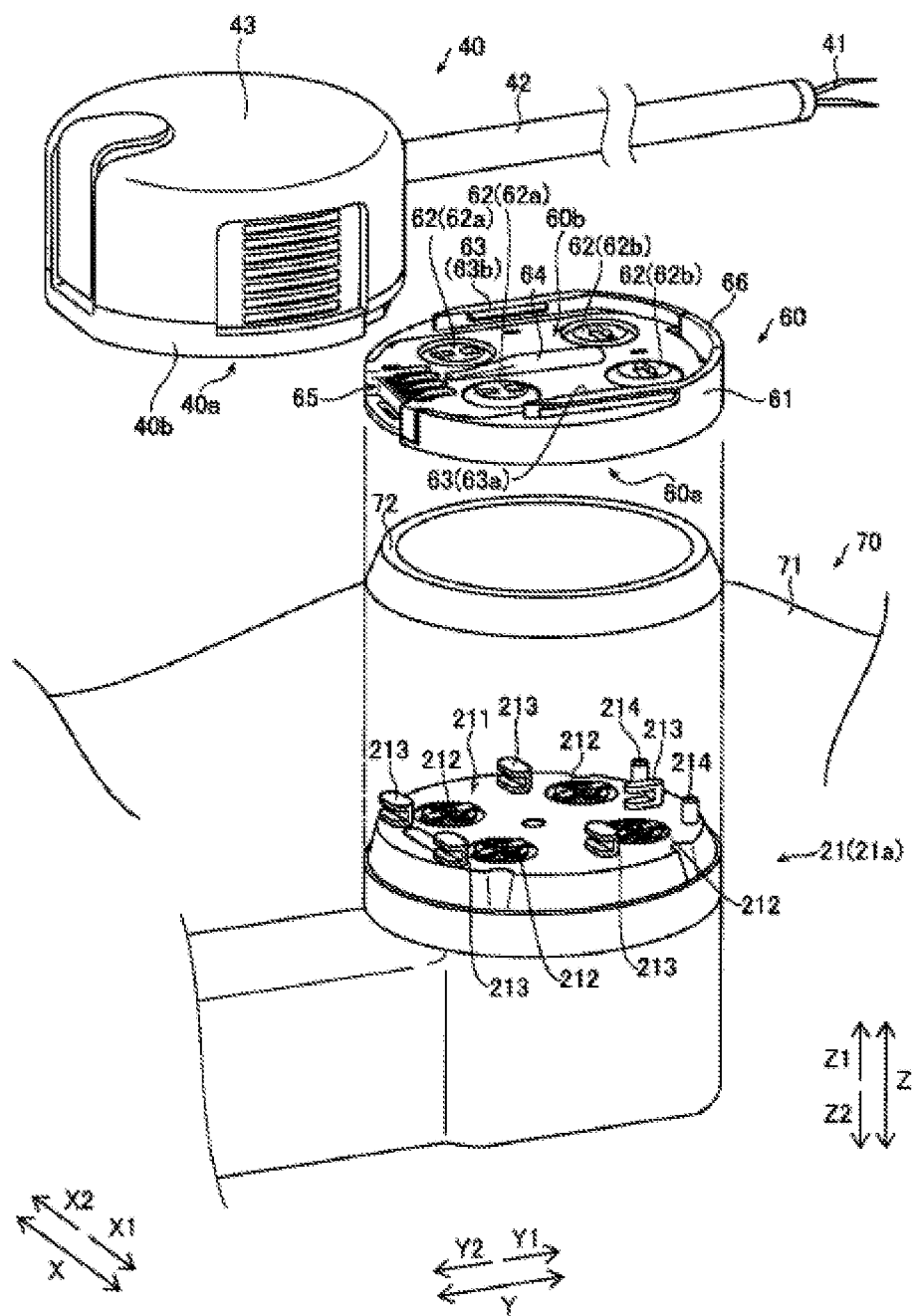
FIG. 4 is a diagram illustrating a perspective view of a state of an embodiment where the adaptor and the surgical instrument are detached from the robot arm.
Figure 5:
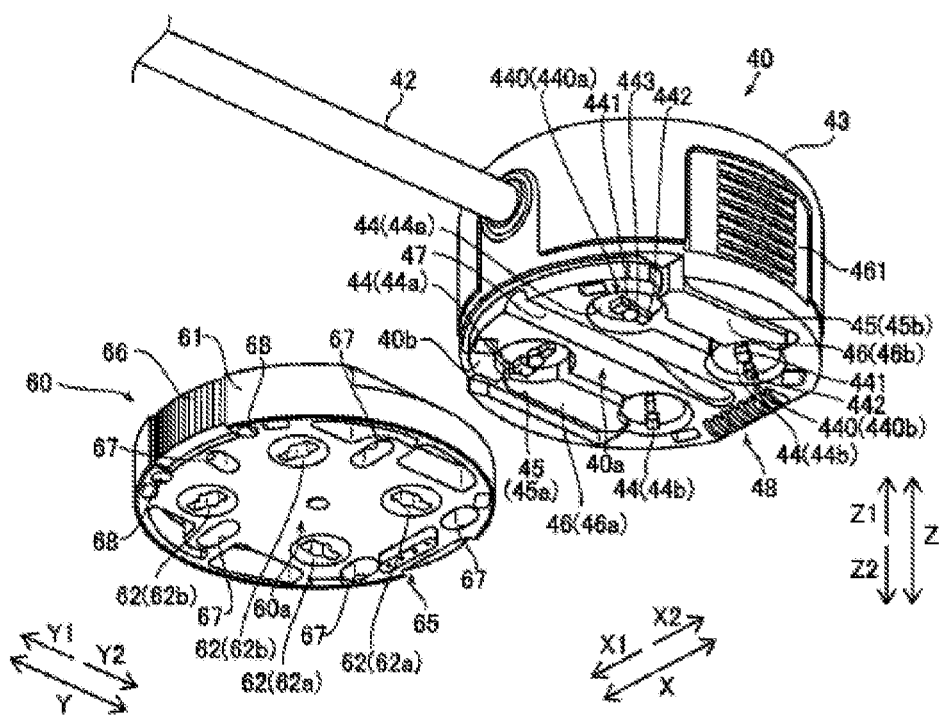
FIG. 5 is a diagram illustrating a perspective view of the surgical instrument and the adaptor according to an embodiment as seen from below.

As illustrated in FIG. 4, the adaptor 60 includes a base body 61, drive transmission members 62, guide rails 63, a precedence guide rail 64, a first electrode array 65, and an arm engagement portion 66. As illustrated in FIG. 5, the adaptor 60 includes arm engagement holes 67 and positioning holes 68. As illustrated in FIG. 4, the drive transmission members 62 include first drive transmission members 62a arranged in the Y2 side and second drive transmission members 62b arranged in the Y1 side. In the adaptor 60, a first surface 60a is arranged in the Z2 side and attached to the robot arm 21a. The adaptor 60 includes a second surface 60b arranged in the Z1 side to which the surgical instrument 40 is attached.

The surgical instrument 40 is a surgical instrument that is detachably connected to the robot arm 21a of the robotic surgical system 100 through the adaptor 60. As illustrated in FIG. 5, an attachment surface 40a arranged in the Z2 side of the housing 43 of the surgical instrument 40 is attached to the adaptor 60. The surgical instrument 40 includes driven members 44, two guide grooves 45 (a first guide groove 45a and a second guide groove 45b), two movable members 46 (a first movable member 46a and a second movable member 46b), a precedence guide groove 47, and a second electrode array 48. The driven members 44 include first driven members 44a arranged in the Y1 side and second driven members 44b arranged in the Y2 side. The surgical instrument 40 includes a base body 40b that includes the attachment surface 40a relative to the adaptor 60.

As illustrated in FIG. 4, the drape 70 includes a body part 71 and an attachment section 72. The body part 71 is made in a film form. The attachment section 72 is made by resin molding. The attachment section 72 includes a through-opening in a section where the robot arm 21a is engaged with the adaptor 60. The through-opening may be provided corresponding to the engagement portion. Through-openings may be provided corresponding to plural engagement portions.

The adaptor 60 is attached to an adaptor attachment surface 211 of the robot arm 21. The robot arm 21 includes rotation drive parts 212, engagement portions 213, and bosses 214.

Figure 10:
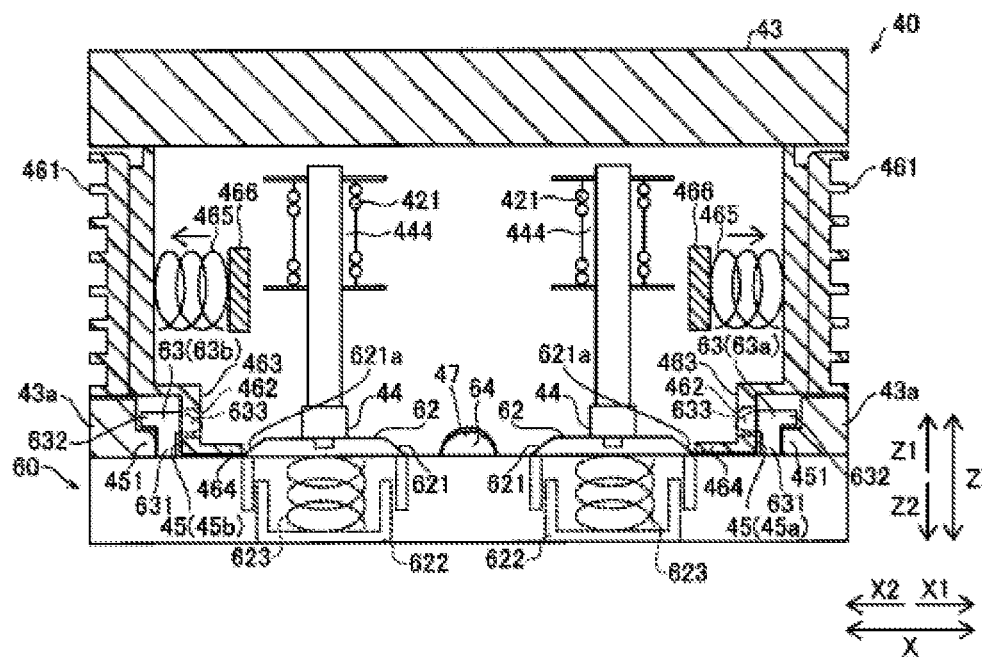
FIG. 10 is a diagram illustrating a first explanatory view of movement of the movable member of the surgical instrument according to an embodiment.

As illustrated in FIG. 5, the driven members 44 of the surgical instrument 40 are rotated and driven and drive the end effector 41. Specifically, in the shaft 42, one end (an end portion on the Y2 side) is connected to the base body 40b, and the other end (an end portion on the Y1 side) is connected to the end effector 41. As illustrated in FIG. 10, the driven members 44 are connected to the end effector 41 with wires 421 inserted through the shaft 42. Specifically, the driven members 44 are rotatably provided on the base body 40b. End portions of the wires 421 operating the end effector 41 are connected to the driven members 44, respectively. With the driven members 44 rotated, the wires 421 are drawn and the end effector 41 is driven. In the housing 43, the driven members 44 are connected by the shaft 42 and gears. Specifically, the housing 43 is provided on the base body 40b to cover the driven members 44. With the driven members 44 rotated, the shaft 42 is rotated. The wires 421 are an example of elongated elements.

As illustrated in FIG. 5, for example, four driven members 44 are provided. The shaft 42 is rotated by the rotation of one of the driven members 44, and the end effector 41 is driven by the rotation of the other three driven members 44. The four driven members 44 are arranged such that two of them are arranged in the X direction while two of them are arranged in the Y direction.

Figure 6:
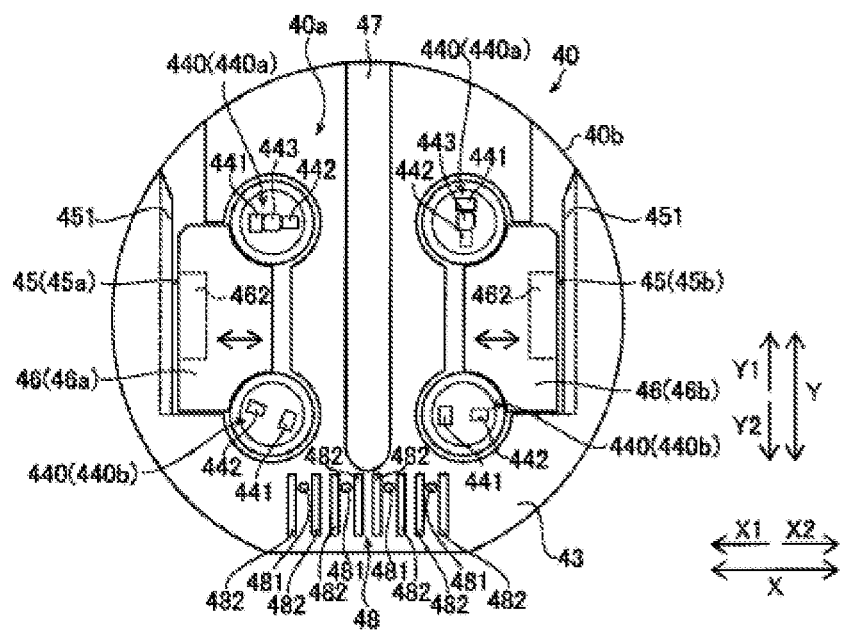
FIG. 6 is a diagram illustrating a view of an attachment surface of the surgical instrument according to an embodiment as seen from below.

As illustrated in FIGS. 5 and 6, the driven members 44 respectively include engagement portions 440 that are engaged with the corresponding drive transmission members 62 provided in the adaptor 60. The engagement portion 440 includes a first engagement portion 440a and a second engagement portion 440b. The first engagement portion 440a is provided in the first driven member 44a of the driven members 44 located on the upstream side (the Y1 side) in a slide insertion direction. The second engagement portion 440b is provided in the second driven member 44b of the driven members 44 located on the downstream side (the Y2 side) in the slide insertion direction. The first engagement portion 440a and the second engagement portion 440b have different shapes. The first engagement portion 440a is engaged with the second drive transmission member 62b of the adaptor 60. The second engagement portion 440b is engaged with the first drive transmission member 62a of the adaptor 60. This makes it possible to prevent the first driven member 44a from being engaged and stuck with the first drive transmission member 62a corresponding to the second driven member 44b during the sliding of the surgical instrument 40 with respect to the adaptor 60. Thus, it is possible to attach the surgical instrument 40 to the adaptor 60 smoothly.

Specifically, the first engagement portion 440a is formed in a shape that avoids the engagement with the drive transmission member 62 (the first drive transmission member 62a) that is engaged with the second engagement portion 440b. This makes it possible to more reliably prevent the first driven member 44a from being engaged and stuck with the first drive transmission member 62a corresponding to the second driven member 44b during the sliding of the surgical instrument 40 with respect to the adaptor 60.

Specifically, the first engagement portion 440a includes a first projection 441, a second projection 442 provided separately from the first projection 441, and a third projection 443 arranged between the first projection 441 and the second projection 442. The second engagement portion 440b includes no third projection 443 but the first projection 441 and the second projection 442. As the common parts are used to constitute the first projection 441 and the second projection 442, the first rotation members 44a and the second rotation members 44b can be formed in different shapes depending on only whether there is the third projection 443. Thus, it is possible to prevent increase of parts types.

The first guide groove 45a and the second guide groove 45b are provided on the attachment surface 40a of the base body 40b. The first guide groove 45a and the second guide groove 45b are provided to respectively receive a first guide rail 63a and a second guide rail 63b provided on the adaptor 60 by sliding. The guide grooves 45 are provided to extend along the Y direction. Two guide grooves 45 are provided to be opposed to each other in the X direction. The first guide groove 45a and the second guide groove 45b are provided substantially parallel to each other. The first guide rail 63a and the second guide rail 63b of the adaptor 60 are respectively inserted into the first guide groove 45a and the second guide groove 45b, and the first guide groove 45a and the second guide groove 45b thus guide attachment of the surgical instrument 40 to the adaptor 60. As illustrated in FIG. 6, the first guide groove 45a and the second guide groove 45b include insertion sections (end portions on the Y1 side) for the first guide rail 63a and the second guide rail 63b, and the insertion sections are formed with groove widths wider than the rest of the first and second guide grooves and gradually get wider as extending in the Y1 direction or gradually get narrower as extending in the Y2 direction. The first guide groove 45a and the second guide groove 45b can be introduced easily to the first guide rail 63a and the second guide rail 63b of the adaptor 60. Consequently, it is possible to attach the surgical instrument 40 to the adaptor 60 easily.

In an embodiment, the first guide groove 45a is formed of the base body 40b and the first movable member 46a. The second guide groove 45b is formed of the base body 40b and the second movable member 46b. The first movable member 46a and the second movable member 46b are provided movably with respect to the housing 43 and the base body 40b. The first movable member 46a and the second movable member 46b are configured to be moved and vary groove widths of the guide grooves 45. Specifically, the width of each guide groove 45 is varied according to movement in the X direction of the corresponding movable member 46. Specifically, when the movable member 46 is moved inward, the width of the guide groove 45 is increased. When the movable member 46 is moved outward, the width of the guide groove 45 is decreased. The movable member 46 is biased to a direction (an outward direction) in which the width of the guide groove 45 is decreased.

The groove widths of the guide grooves 45 can be varied by moving the movable members 46. Consequently, it is possible to easily attach and detach the surgical instrument 40 to and from the adaptor 60 by sliding the guide grooves 45 having the increased groove widths with respect to the guide rails 63 of the adaptor 60. Additionally, the base body 40b of the surgical instrument 40 can be engaged with and fixed to the adaptor 60 by decreasing the groove widths of the guide grooves 45 after inserting the guide rails 63 of the adaptor 60 in the guide grooves 45. Consequently, it is possible to stably fix the surgical instrument 40 to the adaptor 60. Therefore, in the surgical instrument 40 that is detachably connected to the robot arm 21a of the robotic surgical system 100 through the adaptor 60, the surgical instrument 40 can be easily attached to and detached from the adaptor 60 and the surgical instrument 40 can be stably fixed to the adaptor 60.

The precedence guide groove 47 is provided to extend along the Y direction. The precedence guide groove 47 is provided between the first guide groove 45a and the second guide groove 45b. The precedence guide groove 47 is formed to extend substantially parallel to the first guide groove 45a and the second guide groove 45b. The precedence guide groove 47 is provided in the substantial center in the X direction of the attachment surface 40a.

The second electrode array 48 is connected to the robot arm 21 through the first electrode array 65 of the adaptor 60. The second electrode array 48 is connected to a board provided in the housing 43. Specifically, the board of the surgical instrument 40 is connected to the robot arm 21 by attaching the surgical instrument 40 to the robot arm 21 through the adaptor 60. The board in the housing 43 is used for, for example, managing types of the surgical instrument 40 and the number of uses of the surgical instrument 40.

As illustrated in FIG. 6, the second electrode array 48 on the attachment surface 40a of the surgical instrument 40 includes electrodes 481 and the protrusions 482. The electrodes 481 are respectively connected with the electrodes 651 of the first electrode array 65 of the adaptor 60. The protrusions 482 are formed near the electrodes 481 and protrude from the attachment surface 40a. The protrusions 482 are located in two sides in the X direction of each electrode 481. The protrusions 482 are provided for preventing hand touch on the electrode 481. Specifically, an interval between the protrusions 482 sandwiching the electrode 481 is sufficiently smaller than the finger size. The protrusion 482 protrudes in the Z direction more than the electrode 481 does. Even when the surgical instrument 40 is detached from the adaptor 60, the protrusion 482 can prevent the worker from touching the second electrode array 48.

As illustrated in FIG. 4, the adaptor 60 is provided to detachably connect the surgical instrument 40 to the robot arm 21a of the robotic surgical system 100. As illustrated in FIGS. 4 and 5, the base body 61 includes the first surface 60a to be attached to the robot arm 21a and the second surface 60b to which the attachment surface 40a of the surgical instrument 40 is mounted. The adaptor 60 has the substantially same size with the housing 43 of the surgical instrument 40 as seen in the Z direction. Specifically, the adaptor 60 is formed in a substantially circular shape having the substantially same diameter as the diameter of the housing 43 as seen in the Z direction.

The drive transmission members 62 are rotatably provided in the base body 61. Specifically, the drive transmission members 62 are provided rotatably about rotation axes extending in the Z direction. The drive transmission members 62 transmit driving force of the rotation drive parts 212 of the robot arm 21a to the driven members 44 of the surgical instrument 40. Plural drive transmission members 62 are provided corresponding to the driven members 44 of the surgical instrument 40. The drive transmission members 62 are respectively arranged in positions corresponding to the driven members 44 of the surgical instrument 40.

Figure 7:
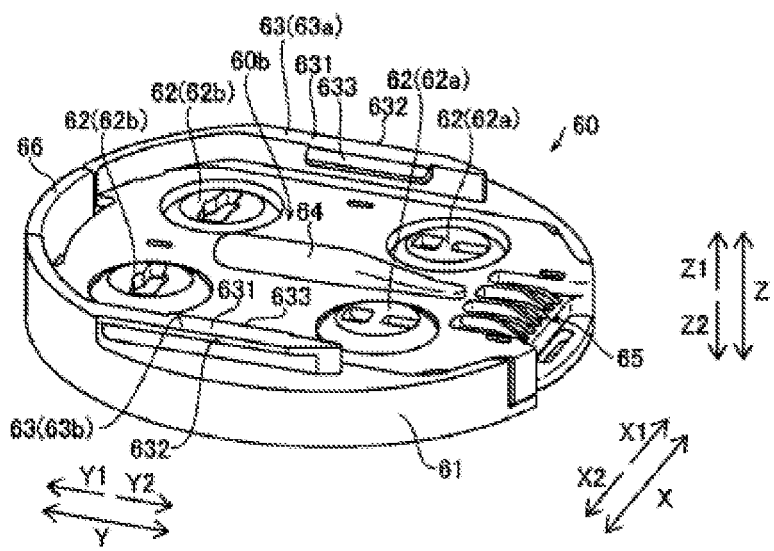
FIG. 7 is a diagram illustrating a perspective view of the adaptor according to an embodiment as seen from above.

As illustrated in FIG. 7, the guide rails 63 are provided on the second surface 60b. The guide rails 63 are provided to extend along the Y direction. The two guide rails 63 are provided to be opposed to each other in the X direction. The first guide rail 63a and the second guide rail 63b are provided substantially parallel to each other. The first guide rail 63a and the second guide rail 63b are provided correspondingly to the first guide groove 45a and the second guide groove 45b that are provided substantially parallel to each other on the attachment surface 40a of the surgical instrument 40. The first guide rail 63a and the second guide rail 63b of the second surface 60b are configured to make sliding, in the Y direction, the first and second guide grooves 45a and 45b of the attachment surface 40a and guide the surgical instrument 40 such that the drive transmission members 62 correspond to the driven members 44 provided on the attachment surface 40a.

The first guide rail 63a and the second guide rail 63b of the second surface 60b are configured to guide the first guide groove 45a and the second guide groove 45b of the surgical instrument 40 in a direction (the Y direction) crossing a direction (the Z direction) in which a second member 622 moves with respect to a first member 621. Specifically, a direction in which the surgical instrument 40 is slid and inserted into the adaptor 60 is substantially parallel to a direction in which the shaft 42 of the surgical instrument 40 extends.

The precedence guide rail 64 is provided on the second surface 60b. The precedence guide rail 64 is provided to extend along the Y direction. The precedence guide rail 64 is provided between the first guide rail 63a and the second guide rail 63b. The precedence guide rail 64 is formed to extend substantially parallel to the first guide rail 63a and the second guide rail 63b. The precedence guide rail 64 is provided in the substantial center in the X direction of the second surface 60b. The precedence guide rail 64 is provided correspondingly to the precedence guide groove 47 provided on the attachment surface 40a. Specifically, the precedence guide rail 64 guides the surgical instrument 40 before the first guide rail 63a and the second guide rail 63b guide the surgical instrument 40.

A portion of the precedence guide rail 64 in the upstream side (the Y2 side) in a slide insertion direction in which the surgical instrument 40 is slid and inserted into the adaptor 60 is formed in a tapered shape. Specifically, the precedence guide rail 64 is formed such that an end portion at the Y2 side has a width tapered in the X direction. The precedence guide rail 64 is formed such that the end portion in the Y2 side has a height tapered in the Z direction.

The first electrode array 65 is connected to the second electrode array 48 of the surgical instrument 40 and the robot arm 21.

As illustrated in FIGS. 4 and 5, the arm engagement portion 66 is engaged with the engagement portions 213 of the robot arm 21. Specifically, the arm engagement portion 66 is engaged with the engagement portions 213 that are inserted in the arm engagement holes 67 provided in the first surface 60a. The arm engagement portion 66 can be moved in the Y direction. The arm engagement portion 66 is biased in the Y1 direction by a bias member. The engagement of the arm engagement portion 66 with the engagement portions 213 is made by moving the arm engagement portion 66 in the Y1 direction. On the other hand, the engagement of the arm engagement portion 66 with the engagement portions 213 is released by moving the arm engagement portion 66 in the Y2 direction.

Plural arm engagement holes 67 are provided. Specifically, the adaptor 60 is fixed to the robot arm 21 by engagement of plural portions. For example, five arm engagement holes 67 are provided. The arm engagement holes 67 are provided at equal intervals along a circumferential direction of the first surface 60a.

The positioning holes 68 are provided in the first surface 60a. The bosses 214 of the robot arm 21 are fitted to the positioning holes 68. Plural positioning holes 68 are provided. The positioning holes 68 are provided near an end portion in the Y1 side of the first surface 60a.

As illustrated in FIG. 7, each guide rail 63 includes a rail part 631, a jut part 632, and a tab part 633. The rail part 631 is formed to extend in the Y direction. The rail part 631 slides into the guide groove 45 of the surgical instrument 40 and guides the movement of the surgical instrument 40 with respect to the adaptor 60.

The jut part 632 is formed to jut in the X direction from the rail part 631. Specifically, the jut part 632 of the first guide rail 63a (the guide rails 63 in the X1 side) is arranged in the X1 side of the rail part 631. The jut part 632 of the second guide rail 63b (the guide rails 63 in the X2 side) is arranged in the X2 side of the rail part 631.

The tab part 633 is formed to jut in the X direction from the rail part 631. Specifically, the tab part 633 which is included in the first guide rail 63a (the guide rails 63 in the X1 side) is arranged in the X2 side of the rail part 631. The tab part 633 which is included in the second guide rail 63b (the guide rails 63 in the X2 side) is arranged in the X1 side of the rail part 631. Specifically, the jut part 632 is provided to the rail part 631 on the opposite side of the tab part 633. The jut part 632 is arranged in the outer side in the X direction of the rail part 631. The tab part 633 is arranged in the inner side in the X direction of the rail part 631.

The jut part 632 is engaged with a restriction portion 451 (see FIGS. 10 and 11) provided in the guide groove 45 of the surgical instrument 40. The engagement of the jut part 632 with the restriction portion 451 enables rigid connection between the surgical instrument 40 and the adaptor 60 and prevents detachment of the surgical instrument 40 from the adaptor 60 in the Z direction.

The tab part 633 is engaged with an engagement hole 462 (see FIGS. 9 to 11) provided in the guide groove 45 of the surgical instrument 40. Specifically, the tab part 633 is engaged with the engagement hole 462 provided in a side wall 463 of the movable member 46 forming the guide groove 45. The engagement of the tab part 633 with the engagement hole 462 enables positioning and fixing of the surgical instrument 40 guided by the guide rail 63 with respect to the adaptor 60. Specifically, the engagement of the tab part 633 with the engagement hole 462 enables positioning of the surgical instrument 40 in the Y direction with respect to the adaptor 60 and fixing (locking) of the surgical instrument 40 to the adaptor 60 to prevent detachment of the surgical instrument 40 in the Y direction. As illustrated in FIG. 10, the tab part 633 is formed to be inclined along the X direction.

Figure 8:
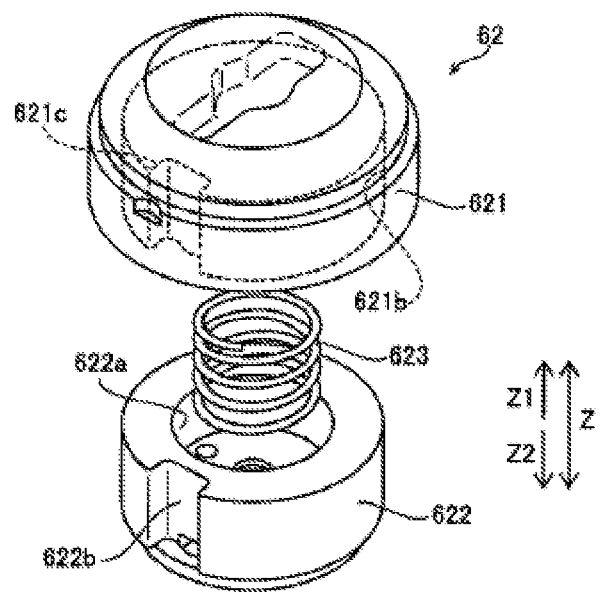
FIG. 8 is a diagram illustrating an exploded perspective view of a drive transmission member of the adaptor according to an embodiment.

As illustrated in FIG. 8, each drive transmission member 62 includes the first member 621 and the second member 622. The second member 622 is provided movably with respect to the first member 621 with a bias member 623 interposed in between. The first member 621 includes a recess portion 621b and an engagement portion 621c. The recess portion 621b receives the second member 622 fitted thereto. The engagement portion 621c is engaged with the second member 622. The second member 622 includes a recess portion 622a and an engagement portion 622b. The recess portion 622a houses the bias member 623. The engagement portion 622b is engaged with the first member 621. The first member 621 and the second member 622 are fitted to each other in the Z direction with the bias member 623 interposed in between. The first member 621 is positioned in the second surface 60b side (the Z1 side). The second member 622 is positioned in the first surface 60a side (the Z2 side). The bias member 623 biases the first member 621 toward the Z1 side with respect to the second member 622. For example, a spring constitutes the bias member 623.

The second member 622 is arranged flush with the first surface 60a in the Z direction. The second member 622 is arranged so as not to move with respect to the base body 61 in the Z direction. The first member 621 is arranged movably with respect to the base body 61 in the Z direction. This makes it possible to move the first member 621 of the drive transmission member 62 downward in the Z direction to prevent interference with the movement of the surgical instrument 40 when attaching the surgical instrument 40 to the adaptor 60 by the guiding along the first guide rail 63a and the second guide rail 63b. Specifically, the first guide groove 45a and the second guide groove 45b are configured to guide the guide rails 63 in a direction (the Y direction) crossing a direction (the Z direction) in which the driven member 44 is engaged with the drive transmission member 62. In this case, the first member 621 of the drive transmission member 62 can be moved so as not to obstruct the movement of the surgical instrument 40 when guiding the surgical instrument 40 along the guide rails 63 and attaching the surgical instrument 40 to the adaptor 60.

The first member 621 is configured to rotate in accordance with the rotation of the second member 622 about the rotation axis in the Z direction. Specifically, the first member 621 is configured such that the engagement portion 621c provided in an inner circumferential portion of the first member 621 and the engagement portion 622b provided in an outer circumferential portion of the second member 622 are engaged with each other. The engagement portion 621c of the first member 621 is formed to protrude inward from the recess portion 621b. The engagement portion 622b of the second member 622 is formed to be recessed inward from the outer circumferential portion of the second member 622. The engagement portion 621c of the first member 621 and the engagement portion 622b of the second member 622 are configured to be engaged with each other even when the first member 621 is moved with respect to the second member 622 in the Z direction. Specifically, the first member 621 is configured to be rotated with the second member 622 regardless of a location of the first member 621 with respect to the second member 622 in the Z direction. When the second member 622 is rotated in accordance with the rotation of the rotation drive part 212 of the robot arm 21, the first member 621 is rotated together. Consequently, the rotation of the rotation drive part 212 of the robot arm 21 is transmitted to the driven member 44 of the surgical instrument 40 engaged with the first member 621.

Figure 9:
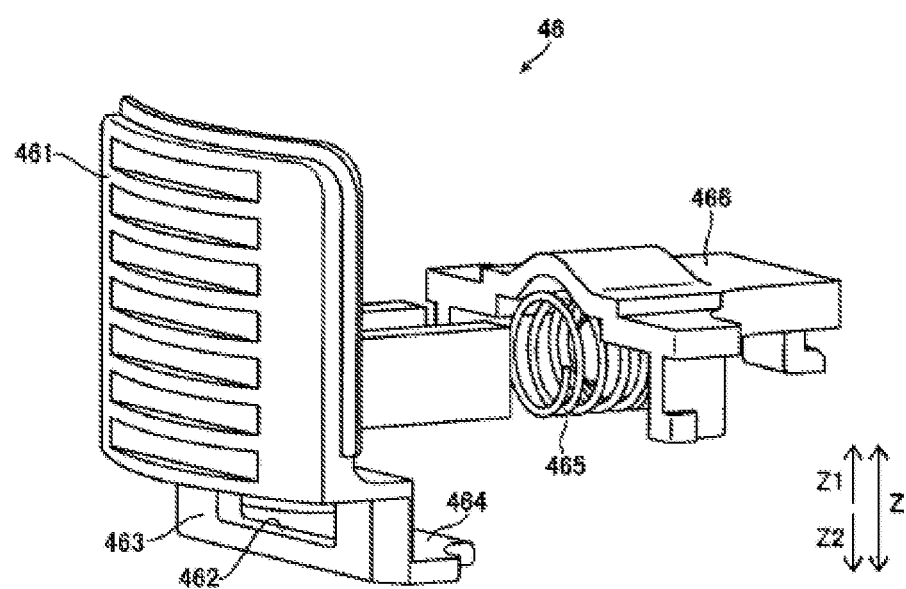
FIG. 9 is a diagram illustrating an exploded perspective view of a movable member of the surgical instrument according to an embodiment.
Figure 11:
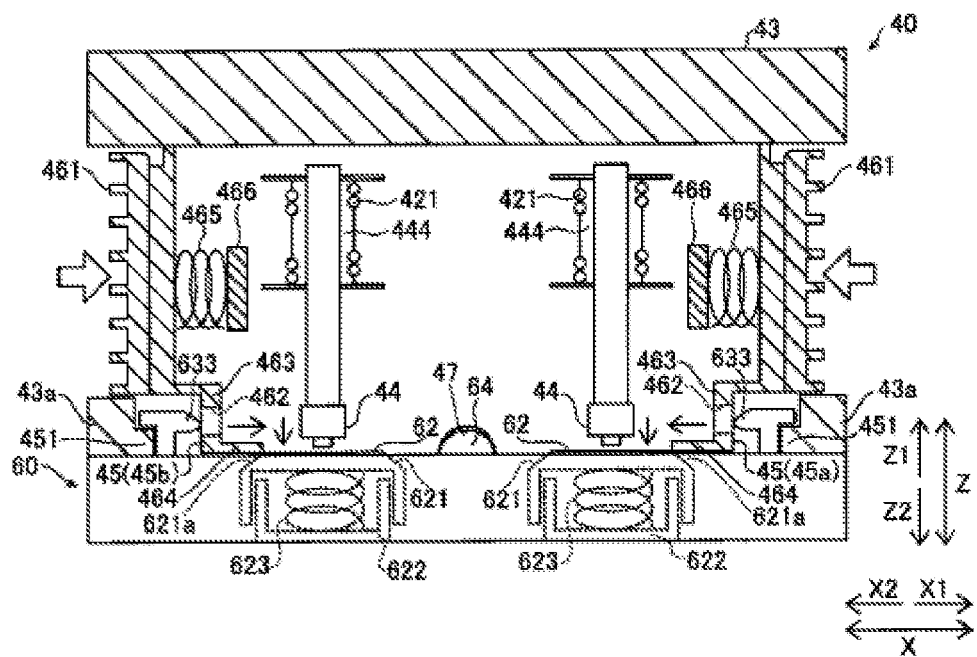
FIG. 11 is a diagram illustrating a second explanatory view of movement of the movable member of the surgical instrument according to an embodiment.

As illustrated in FIG. 9, each movable member 46 of the surgical instrument 40 includes a button 461, the engagement hole 462, the side wall 463, a press-down part 464, a bias member 465, and a fixed member 466 or a stationary member. As illustrated in FIGS. 10 and 11, the movable members 46 are biased in directions (outward directions) in which the widths of the guide grooves 45 are decreased by the bias members 465. The movable members 46 are moved in directions (inward directions) in which the widths of the guide grooves 45 are increased when the worker presses the buttons 461. Specifically, the first movable member 46a (the movable member 46 on the X1 side) is biased in the X1 direction by the corresponding bias member 465. The first movable member 46a (the movable member 46 on the X1 side) is moved in the X2 direction against the bias force by being pressed toward the X2 side. On the other hand, the second movable member 46b (the movable member 46 on the X2 side) is biased in the X2 direction by the corresponding bias member 465. The second movable member 46b (the movable member 46 on the X2 side) is moved in the X1 direction against the bias force by being pressed toward the X1 side.

As illustrated in FIGS. 6, 10, and 11, the movable member 46 is configured to increase the groove width of the guide groove 45 by being pressed and moved. It is possible to increase the groove width of the guide groove 45 easily with the worker pressing the movable member 46.

The button 461 is provided to be pressed and operated by the worker. As illustrated in FIG. 5, the button 461 is provided on the outer side in the X direction so as to be exposed from the housing 43. Grooves along the Y direction are formed on the button 461. This makes it possible to recognize the button 461 only by touching the position of the button 461 and also to suppress slipping of the hand of the operator.

The engagement hole 462 is engaged with the tab part 633 provided on the guide rail 63 of the adaptor 60. As illustrated in FIG. 9, the engagement hole 462 is formed in the side wall 463. As illustrated in FIGS. 10 and 11, the engagement hole 462 is formed to pass through the side wall 463 in the X direction. This allows the positioning and fixing to the adaptor 60 of the surgical instrument 40 that is guided by the guide rail 63.

As illustrated in FIG. 11, the movable member 46 is configured to disengage the engagement hole 462 from the tab part 633, that is, the engagement of the surgical instrument 40 with the adaptor 60 by being moved to increase the groove width of the guide groove 45. The operation of increasing the groove width of the guide groove 45 and the operation of disengaging the engagement hole 462 from the tab part 633 of the adaptor 60 can be performed at the same time. Consequently, it is possible to detach the surgical instrument 40 from the adaptor 60 easily.

The side wall 463 constitutes an inner wall in the X direction of the guide groove 45. Specifically, as illustrated in FIGS. 10 and 11, the side wall 463 is arranged to face the restriction portion 451 provided on the base body 40b. The guide groove 45 formed of the side wall 463 and the restriction portion 451 sandwiches the rail part 631 of the guide rail 63 and guides the guide rail 63.

The restriction portion 451 is provided on the base body 40b side of each of the first guide groove 45a and the second guide groove 45b. The restriction portion 451 is formed to extend in the Y direction. The restriction portion 451 is engaged with the jut part 632 provided on the guide rail 63 and jutting in a direction (the X direction) parallel to the attachment surface 40a, and limits the movement of the attachment surface 40a with respect to the adaptor 60 in a direction (the Z direction) of the rotation axis of the driven member 44. Since the jut part 632 is engaged with the restriction portion 451 and the movement in the direction (the direction orthogonal to the attachment surface 40a) of the rotation axis of the driven member is limited, it is possible to stably fix the surgical instrument 40 to the adaptor 60.

As illustrated in FIGS. 10 and 11, when the movable member 46 are moved to increase the groove width of the guide groove 45, the press-down part 464 disengages the drive transmission members 62 from the driven members 44 by moving the first members 621 of the drive transmission members 62 in a direction (the Z2 direction) away from the driven members 44. With this configuration, the operation of increasing the groove width of the guide groove 45 and the operation of disengage the driven members 44 from the drive transmission members 62 can be performed at the same time. Consequently, it is possible to detach the surgical instrument 40 from the adaptor 60 easily.

Specifically, the press-down part 464 is configured to disengage the drive transmission members 62 from the driven members 44 by being moved in the direction (the X direction) crossing the direction in which the driven members 44 are engaged with the drive transmission members 62, along with the movement of the movable member 46. Accordingly, it is possible to disengage the driven members 44 from the drive transmission members 62 with the worker operating the movable member 46 to increase the groove width of the guide groove 45 in the direction (the X direction) crossing the direction in which the driven members 44 are engaged with the drive transmission members 62.

Specifically, along with the movement of the movable member 46, the press-down part 464 is configured to run onto tapered portions 621a provided on the first members 621 and to move the first members 621 in the direction (the Z2 direction) away from the driven members 44. With this configuration, even when the movement direction of the press-down part 464 and the direction in which the driven members 44 are engaged with the drive transmission members 62 are different, it is possible to disengage the driven members 44 from the drive transmission members 62 easily by the movement of the press-down part 464.

The press-down part 464 is connected to an inner side in the X direction of a lower portion of the side wall 463. The press-down part 464 is formed in a plate shape extending in the XY plane. The press-down part 464 includes recesses in portions corresponding to the driven members 44.

The bias member 464 is configured to bias the button 461, the side wall 463, and the press-down part 464 outward in the X direction. An inner end portion of the bias member 465 is put in contact with the fixed member 466, and thus the inward movement of thereof in the X direction is limited. An outer end portion of the bias member 465 is put in contact with an inner side of the button 461 and biases the button 461, the side wall 463, and the press-down part 464 outward in the X direction. For example, a spring constitutes the bias member 623.

As illustrated in FIGS. 10 and 11, the restriction portion 451 is provided in the guide groove 45 of the attachment surface 40a of the surgical instrument 40. The restriction portion 451 is formed to extend in the Y direction along the guide groove 45. The jut part 632 of the guide rail 63 provided on the second surface 60b of the adaptor 60 is engaged with the restriction portion 451.

The tab part 633 of the guide rail 63 provided on the second surface 60b of the adaptor 60 is engaged with the engagement hole 462. The engagement hole 462 is provided in the side wall 463 of the movable member 46 forming the guide groove 45. When moving the movable member 46 inward in the X direction, the engagement of the tab part 633 with the engagement hole 462 is released. Further, when moving the movable member 46 inward in the X direction, the drive transmission member 62 is pushed down in the Z2 direction, which release the engagement of the drive transmission member 62 with the driven member 44. In this state, the surgical instrument 40 can be detached from the adaptor 60 by sliding the surgical instrument 40 in the Y2 direction with respect to the adaptor 60.

Figure 12:
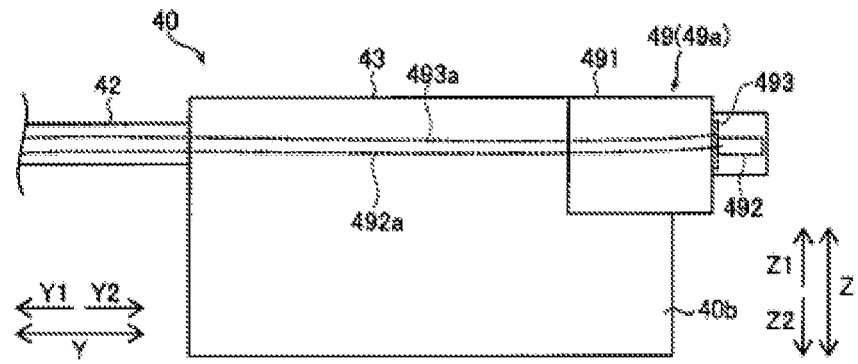
FIG. 12 is a diagram illustrating a view of an example of the surgical instrument including a bipolar connector according to an embodiment.
Figure 13:
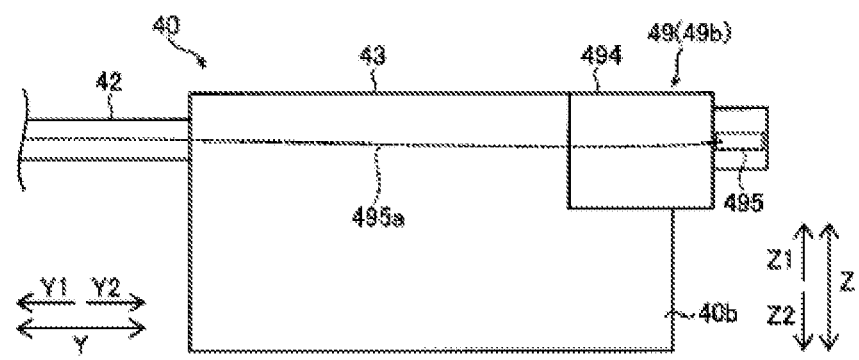
FIG. 13 is a diagram illustrating a view of an example of the surgical instrument including a monopolar connector according to an embodiment.
Figure 14:
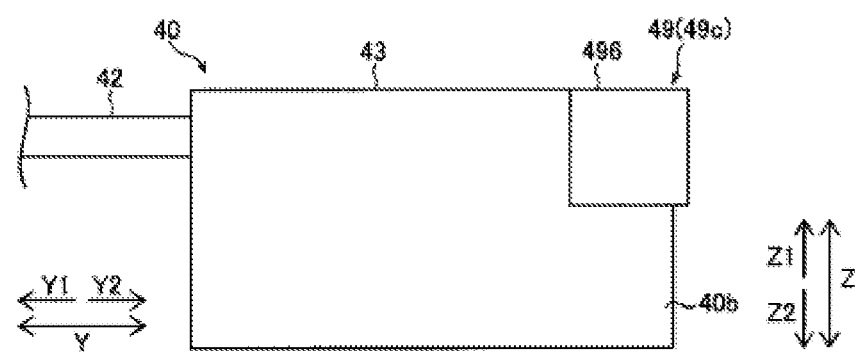
FIG. 14 is a diagram illustrating a view of an example of the surgical instrument including a non-energization connector according to an embodiment.

As illustrated in FIGS. 12 to 14, a connector 49 or a connecting member is detachably attachable to the base body 40b and is attached to the base body 40b depending on whether there is energization to the end effector 41 (the surgical tool) or depending on the type of the energization. Plural types of the surgical instruments 40 can be assembled by changing the connector 49 depending on whether there is energization to the end effector 41 (the surgical tool) or depending on the type of the energization. Consequently, it is possible to use the members such as the base body 40b, the housing 43, the driven member 44, and the movable member 46 commonly in the plural types of the surgical instruments 40.

For example, depending on the type of the end effector 41, the connector 49 may be a monopolar connector 49b (see FIG. 13), a bipolar connector 49a (see FIG. 12), or a non-energization connector 49c (see FIG. 14). That is, the connector 49 can be changed between the monopolar connector 49b, the bipolar connector 49a, and the non-energization connector 49c depending on whether there is energization to the end effector 41 or depending on the type of the energization. Consequently, it is possible to assemble plural types of the surgical instruments 40.

The connector 49 is configured to be mounted by being slid on the base body 40b and the housing 43. Specifically, the connector 49 is attached to and detached from the base body 40b and the housing 43 by being slid in the Y direction. The sliding allows easy attachment of the connector 49 to the base body 40b and the housing 43.

As illustrated in FIG. 12, the bipolar connector 49a is provided to supply power of a bipolar to the end effector 41. The bipolar connector 49a includes a body part 491, an electrode 492, and an electrode 493. The electrode 492 is connected to wiring 492a. The electrode 493 is connected to wiring 493a. The wiring 492a and 493a are connected to the end effector 41. The body part 491 holds the electrodes 492 and 493. The body part 491 is configured to be attachable to the base body 40b and the housing 43. The electrodes 492 and 493 are configured to be connectable to a connector that is connected to the wiring for power supplying.

As illustrated in FIG. 13, the monopolar connector 49b is provided to supply power of a monopolar to the end effector 41. The monopolar connector 49b includes a body part 494 and an electrode 495. The electrode 495 is connected to wiring 495a. The wiring 495a is connected to the end effector 41. The body part 494 holds the electrode 495. The body part 494 is configured to be attachable to the base body 40b and the housing 43. The electrode 495 is configured to be connectable to a connector that is connected to the wiring for power supplying.

As illustrated in FIG. 14, the non-energization connector 49c is provided to close an opening of the housing 43. Specifically, the housing 43 is provided with the opening for the connection of the bipolar connector 49a or the monopolar connector 49b. When the end effector 41 that does no need power supply is attached to the shaft 42, the opening is covered by the non-energization connector 49c. The non-energization connector 49c includes a body part 496. The body part 496 is configured to be attachable to the base body 40b and the housing 43.

(Attachment of Surgical Instrument to Robot Arm)

Figure 15:
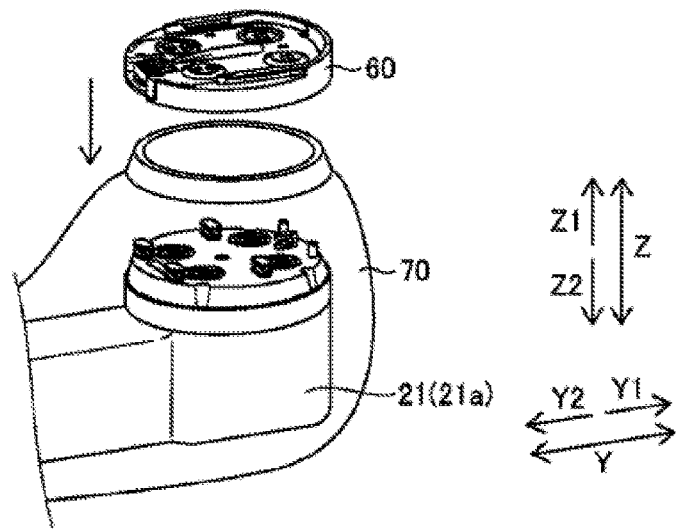
FIG. 15 is a diagram illustrating an explanatory view of attachment of the adaptor to the robot arm according to an embodiment.
Figure 16:
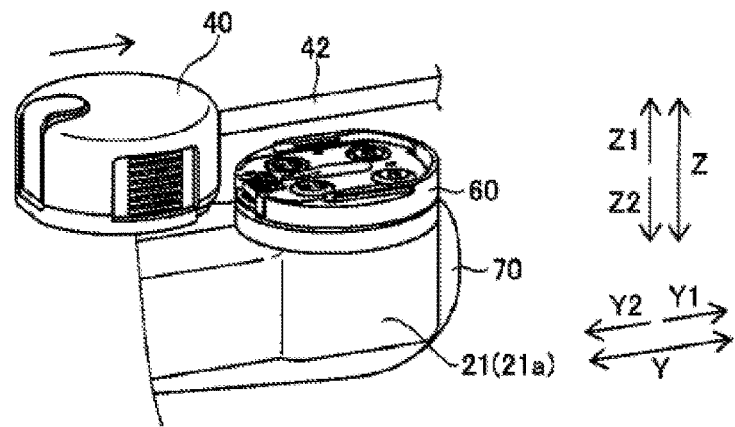
FIG. 16 is a diagram illustrating a first explanatory view of attachment of the surgical instrument to the adaptor according to an embodiment.
Figure 17:
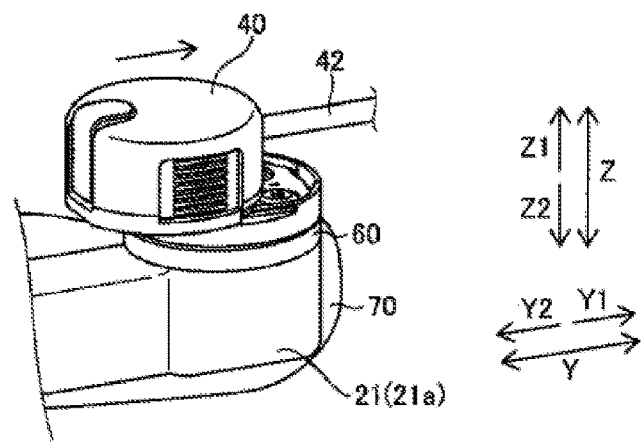
FIG. 17 is a diagram illustrating a second explanatory view of attachment of the surgical instrument to the adaptor according to an embodiment.

With reference to FIGS. 15 to 17, attachment of the surgical instrument 40 to the robot arm 21a according to an embodiment is described.

As illustrated in FIG. 15, the adaptor 60 is attached to the robot arm 21a with covered by the drape 70. The adaptor 60 is moved in the Z direction with respect to the robot arm 21a to be attached to the robot arm 21a. As illustrated in FIGS. 16 and 17, the surgical instrument 40 is attached to the adaptor 60 attached to the robot arm 21a. The surgical instrument 40 is moved in the Y direction along the precedence guide rail 64, the first guide rail 63a, and the second guide rail 63b of the adaptor 60 and thereby attached to the adaptor 60. In this way, the surgical instrument 40 is attached to the robot arm 21a through the adaptor 60.

When detaching the surgical instrument 40 from the robot arm 21a, the surgical instrument 40 is slid and moved in the Y2 direction while pressing the buttons 461 of the movable members 46 of the surgical instrument 40. More specifically, the first guide groove 45a and the second guide groove 45b of the surgical instrument 40 are slid and moved in the Y2 direction along the first guide rail 63a and the second guide rail 63b, and the surgical instrument 40 is thus detached from the adaptor 60.

MODIFICATIONS

It should be understood that the one or more embodiments disclosed herein are illustrated by way of example in every respect and do not limit the invention. The scope of the invention is indicated by claims, not by explanation of the embodiments, and includes equivalents to claims and all alterations (modifications) within the same.

For example, the surgical instrument is attached or detached by being slid and moved in the shaft-extending direction along the second surface of the adaptor in an example illustrated in the above-described one or more embodiments, but the invention is not limited thereto. In an embodiment or a modification, the surgical instrument may be attached or detached by being slid and moved in a direction crossing the shaft-extending direction along the second surface of the adaptor.

The movable members are movable in the direction crossing the shaft-extending direction in an example illustrated in the above-described one or more embodiments, but the invention is not limited thereto. In an embodiment or a modification, the movable members may be movable in the shaft-extending direction, or may be movable in the rotation axis direction of the driven members.

The attachment surface of the surgical instrument is formed in a substantially circular shape in plan view in an example illustrated in the above-described one or more embodiments, but the invention is not limited thereto. In an embodiment or a modification, the shape of the attachment surface of the surgical instrument in plan view may not be a substantially circular shape. For example, the attachment surface of the surgical instrument may be formed in a rectangular shape in plan view.

Four driven members are provided on the base body of the surgical instrument in an example illustrated in the above-described one or more embodiments, but the invention is not limited thereto. In an embodiment or a modification, plural driven members other than four may be provided on the base body of the surgical instrument.

The adaptor and the drape are provided separately in the examples illustrated in the above-described one or more embodiments, but the invention is not limited thereto. In the embodiments or the modifications, the adaptor and drape may be provided integrally.

The invention claimed is:

1. A surgical instrument to be detachably connected to a robot arm of a robotic surgical system through an adaptor, comprising:
   a base body that includes an attachment surface for the adaptor;
   a surgical tool;
   an elongated shaft in which one end is connected to the base body and the other end is connected to the surgical tool;
   driven members that are rotatably provided on the base body and connected with end portions of elongated elements to operate the surgical tool;
   a housing that covers the driven members; and
   a first movable member and a second movable member that are provided movably with respect to the housing and the base body, wherein
   the attachment surface of the base body includes a first guide groove and a second guide groove that slidably receive a first guide rail and a second guide rail provided on the adaptor respectively, and
   the first and second guide grooves are defined by the base body and the first and second movable members such that groove widths of the first and second guide grooves are variable by moving the first and second movable members with respect to the base body.

2. The surgical instrument according to claim 1, wherein the first and second movable members are moved, when pressed, to increase the groove widths of the first and second guide grooves, respectively.

3. The surgical instrument according to claim 1, wherein the adaptor includes drive transmission members that each include a first member and a second member provided movably with respect to the first member with a bias member interposed in between, the drive transmission members being provided to be engaged with the driven members, and
   the first and second movable members respectively include press-down parts that, when the first and second movable members are moved to increase the groove widths of the first and second guide grooves, disengage the drive transmission members from the driven members by moving the first members of the drive transmission members in a direction away from the driven members.

4. The surgical instrument according to claim 3, wherein along with movement of the first and second movable members, the press-down parts disengage the drive transmission members from the driven members by being moved in a direction crossing a direction in which the driven members are engaged with the drive transmission members.

5. The surgical instrument according to claim 3, wherein along with movement of the first and second movable members, the press-down parts run onto tapered portions provided on the first members of the drive transmission members, to move the first members in the direction away from the driven members.

6. The surgical instrument according to claim 3, wherein the first and second guide grooves respectively guide the first and second guide rails of the adaptor in a direction crossing a direction in which the driven members are engaged with the drive transmission members.

7. The surgical instrument according to claim 3, wherein the driven members respectively include engagement portions that are engaged with the corresponding drive transmission members provided on the adaptor,
the engagement portions include a first engagement portion that is provided in a first driven member of the driven members located on an upstream side in a slide insertion direction, and a second engagement portion that is provided in a second driven member of the driven members located on a downstream side in the slide insertion direction and that is formed in a different shape from that of the first engagement portion.

8. The surgical instrument according to claim 7, wherein the first engagement portion is formed in a shape that avoids engagement with the drive transmission member that is engageable with the second engagement portion.

9. The surgical instrument according to claim 7, wherein the first engagement portion includes a first projection, a second projection provided separately from the first projection, and a third projection arranged between the first projection and the second projection, and
the second engagement portion includes a first projection and a second projection having shapes same as the first projection and the second projection of the first engagement portion respectively, without including a third portion having a shape same as the third projection.

10. The surgical instrument according to claim 1, further comprising:
a connector detachably attachable to the base body, wherein the connector comprises a configuration depending on whether the surgical tool is configured to need a power supply or depending on a type of a power supply to the surgical tool.

11. The surgical instrument according to claim 10, wherein
the connector comprises one of a monopolar connector, a bipolar connector, and a non-energization connector.

12. The surgical instrument according to claim 10, wherein
the connector is configured to be mounted by being slid on the base body and the housing.

13. The surgical instrument according to claim 1, wherein the first and second movable members respectively include engagement holes that are engaged with tab parts respectively provided on the first and second guide rails of the adaptor.

14. The surgical instrument according to claim 13, wherein
the first and second movable members disengage the engagement holes from the tab parts on the first and second guide rails of the adaptor when the first and second movable members are moved to increase the groove widths of the first and second guide grooves.

15. The surgical instrument according to claim 13, wherein
restriction portions are formed on base body sides of the first and second guide grooves, wherein the restriction portions are engaged with jut parts, which are respectively provided on the first and second guide rails of the adaptor and projected in a direction parallel to the attachment surface of the base body, and configured to limit movement of the attachment surface with respect to the adaptor in a rotation axis direction of the driven members.

16. The surgical instrument according to claim 1, wherein the first and second guide grooves include insertion sections for the first and second guide rails of the adaptor, and
the insertion sections of the first and second guide grooves are formed with groove widths wider than the rest of the first and second guide grooves.

17. The surgical instrument according to claim 1, further comprising
a second electrode array provided on the attachment surface of the base body and connectable to a first electrode array of the adaptor, and
the second electrode array includes electrodes and protrusions that are provided in the vicinity of the electrodes and protrude from the attachment surface of the base body.

18. The surgical instrument according to claim 1, wherein the surgical instrument is attached to the adaptor that is attached to the robot arm with a drape interposed between the robot arm and the adaptor.

19. A robotic surgical system, comprising:
a robot arm;
an adaptor that is attached to the robot arm; and
a surgical instrument that is attached to the adaptor, wherein
the adaptor includes
a first surface that is attached to the robot arm, a second surface to which the surgical instrument is mounted, and a first guide rail and a second guide rail that are provided on the second surface,
the surgical instrument includes
a base body that includes an attachment surface attached to the second surface of the adaptor,
a surgical tool,
an elongated shaft in which one end is connected to the base body and the other end is connected to the surgical tool,
driven members that are rotatably provided on the base body and connected with end portions of elongated elements operating the surgical tool;
a housing that is provided to cover the driven members; and
a first movable member and a second movable member that are provided movably with respect to the housing and the base body,
the attachment surface of the base body includes a first guide groove and a second guide groove that slidably receive the first guide rail and the second guide rail provided on the adaptor respectively, and
the first and second guide grooves are defined by the base body and the first and second movable members such that groove widths of the first and second guide grooves are variable by moving the first and second movable members with respect to the base body.

20. A method of detaching a surgical instrument that is attached to a robot arm of a robotic surgical system through an adaptor, comprising:

disengaging the surgical instrument from the adaptor by pressing a movable member of the surgical instrument to move the movable member to increase a groove width of a guide groove of the surgical instrument; and detaching the surgical instrument from the adaptor by sliding the guide groove along a guide rail of the adaptor while pressing the movable member of the surgical instrument.

* * * * *